United States Patent [19]

Forster

[11] 4,190,729

[45] Feb. 26, 1980

[54] CARBONYLATION PROCESS WITH STABILIZED CATALYST

[75] Inventor: Denis Forster, St. Louis, Mo.

[73] Assignee: Monsanto Company, St. Louis, Mo.

[21] Appl. No.: 834,074

[22] Filed: Sep. 19, 1977

[51] Int. Cl.$^2$ ............................................. C07C 67/36
[52] U.S. Cl. ..................................... 560/232; 203/6; 203/38; 260/601 R; 560/248; 562/519; 568/594; 568/902; 568/913
[58] Field of Search .............. 560/232, 248, 97, 114, 560/175, 204, 206; 260/532, 601 R, 642 B, 615 A; 203/6, 38; 568/902, 913, 594; 562/519

[56] References Cited

U.S. PATENT DOCUMENTS

| 2,457,204 | 12/1948 | Brook | 560/232 |
| 3,501,518 | 3/1970 | Kutepow et al. | 560/232 |

FOREIGN PATENT DOCUMENTS 39-25031  11/1964  Japan ................................. 560/232

*Primary Examiner*—Vivian Garner
*Attorney, Agent, or Firm*—Joseph D. Kennedy; James W. Williams, Jr.

[57] ABSTRACT

In the cobalt carbonyl-catalyzed carbonylation of methanol to ethanol, acetaldehyde and methyl acetate, a tertiary phosphine oxide is utilized as a stabilizer. Product is distilled from the reaction mixture and the cobalt-containing residue solution is recycled.

17 Claims, No Drawings

CARBONYLATION PROCESS WITH STABILIZED CATALYST

This invention relates to an improved process for carbonylation of methanol. More particularly, it concerns the use of a tertiary phosphine oxide as stabilizer for cobalt carbonyl catalyst in the carbonylation of methanol to ethanol, acetaldehyde and methyl acetate.

BACKGROUND OF THE INVENTION

Cobalt carbonyl is widely used commercially as a catalyst in the oxo process wherein olefins react with carbon monoxide and hydrogen to give aldehyde and alcohols. Cobalt carbonyl is also known to serve as catalyst for the reaction of methanol to give two-carbon molecules such as ethanol, acetaldehyde, and methyl acetate. See *Science,* Vol. 113, page 206 (1951).

The separation of cobalt catalysts from the product of oxo reactions in a form suitable for recycle is usually performed by extraction techniques, which frequently rely upon converting the cobalt catalyst to a water soluble form and then using aqueous extraction for removal from the organic product. In the carbonylation of methanol, such a procedure is not feasible as both methanol and the products are miscible with water. On the other hand direct distillation of the reaction product has the disadvantage that the cobalt catalyst is volatile and unstable and converted to forms which precipitate, coating the distillation equipment with a solid, making recycle impractical. The occurrence of cobalt (II) acetate is also observed, resulting from oxidation of cobalt carbonyl, and the cobalt (II) acetate can precipitate from the distillation heel.

Ethanol, of course, is a material of many known uses. It has recently been proposed that methanol can serve as a starting material for ethylene, being converted to ethanol by reaction with synthesis gas over cobalt catalyst, and subsequently dehydrated to ethylene. The other products of the carbonylation, methyl acetate and acetaldehyde and its acetals, also have recognized uses.

SUMMARY OF THE INVENTION

The present invention involves an improvement in carbonylation of methanol with cobalt catalyst, in which a tertiary phosphine oxide is present. The phosphine oxide allows the reaction to proceed without hindrance, and the product can be distilled without precipitation or loss of the cobalt catalyst, so that the catalyst can be readily recycled to the reactor. This avoids the need for an expensive cobalt recovery and catalyst regeneration scheme. The invention further involves carrying out the carbonylation reaction in the presence of the phosphine oxide, distilling the products, and recycling the distillation heel containing cobalt material for further use as catalyst in carbonylation of additional methanol. In another aspect the invention involves distillation of ethanol from a mixture containing cobalt, ethanol and tertiary phosphine oxide.

DETAILED DESCRIPTION OF THE INVENTION

The present invention involves an improvement in the cobalt-catalyzed carbonylation of methanol. In general procedures used in cobalt-catalyzed carbonylations can be used in the present invention. The improvement is the use of a tertiary phosphine oxide in the product separation, in order to keep the cobalt material in a form in which it will not precipitate, volatilize or otherwise separate from the reaction medium upon heating for distillation or similar procedures. The tertiary phosphine oxides are pentavalent phosphorus compounds with one oxygen atom and three organo substituents on the phosphorus, with the organo substituents being bonded by carbon-to-phosphorus bonds, and the term "tertiary phosphine oxide" as used herein designates such compounds. The organo substituents are generally mainly hydrocarbyl in character, although non-interfering substituents can be present. Halogen, oxygen, nitrogen etc. substituents can often be present without interference. Suitable phosphine oxides can be represented as

$R_3PO$ in which R is an organo substituent of up to 20 or so carbon atoms, bonded to the phosphorus by a carbon-to-phosphorus bond, and is preferably hydrocarbyl. R can, for example, be alkyl, including cycloalkyl, aryl, including alkaryl, etc. and can be such groups as methyl, ethyl, propyl, butyl, isobutyl, hexyl, decyl, phenyl, tolyl, methoxyphenyl, napthyl, cyclohexyl, etc. The R groups on the phosphorus can be the same or different, but are generally the same for convenience. Two of the R groups together can also form a chain to constitute a heterocyclic ring with the phosphorus. A few examples of suitable phosphine oxides are tri-n-butylphosphine oxide, triphenylphosphine oxide, trimethylphosphine oxide, dibutylmethylphosphine oxide, butyldiphenylphosphine oxide, tricyclohexylphosphine oxide, etc. The organo substituents on the phosphorus are generally saturated, such as saturated hydrocarbyl, except for the presence of aromatic unsaturation when aromatic substituents are present. The tertiary phosphine oxide solubilizes various conversion forms of the cobalt catalyst so that the cobalt is kept in solution in the reaction mixture or its distillation residue.

The present invention utilizes a cobalt catalyst, the catalyst being that generally used in cobalt-catalyzed carbonylation reactions. It is generally believed that the effective form of the catalyst comprises cobalt carbonyl. Specifically, the active component of the catalyst in the process of the present invention is believed to be dicobalt octacarbonyl, $Co_2(CO)_8$, and/or cobalt hydrocarbonyl (cobalt tetracarbonyl hydride), $HCo(CO)_4$; however, the direct charging of either of these species is not required. The charging of any cobalt (II) compound which can be converted in situ into dicobalt octacarbonyl and/or cobalt hydrocarbonyl under the reaction conditions employed and which causes no adverse side effects is sufficient. Among the cobalt (II) compounds which may be charged to the reaction vessel, for example, an autoclave, to provide what is believed to be the active form of component of the catalyst of the present invention are cobalt (II) salts, cobalt (II) oxide, and the like. Specific example of cobalt (II) compounds capable of providing the active catalyst of the present invention may be taken from the following non-limiting partial list of suitable cobalt (II) compounds, which partial list includes dicobalt octacarbonyl, cobalt hydrocarbonyl, cobalt (II) acetate, cobalt(II) formate, cobalt (II) propionate, cobalt (II) butanoate, cobalt (II) benzoate, cobalt (II) citrate, cobalt (II) oxalate, cobalt (II) tartrate, cobalt (II) carbonate, cobalt (II) bromide, cobalt (II) chloride, cobalt (II) iodide, cobalt (II) nitrate, cobalt (II) phosphate, cobalt (II)

sulfate, cobalt (II) hydroxide, cobalt (II) oxide, and various hydrates of the above-named compounds, and the like. Various other cobalt carbonyl species in addition to those named may be produced under the reaction conditions, and may, in whole or in part, be effective catalyst components. All such species are referred to herein as "cobalt carbonyl".

The present reaction is carried out in an atmosphere of carbon monoxide and hydrogen. The molar ratio of hydrogen to carbon monoxide may vary widely, with ratios, for example from about 10:1 to about 1:10 being suitable. Often it will be convenient to use approximately equimolar ratios, or whatever ratios are conveniently available in synthesis gas. The reaction to produce ethanol utilizes 2 moles hydrogen per mole of carbon monoxide, but it is not necessary to have the reactants present in stoichiometric ratio. The carbon monoxide contributes to catalyst stability and appreciable carbon monoxide pressure is therefore generally used such as 500 psi to 15000 psi or more, and preferably the reaction is carried out under a total pressure of at least 1500 or 2000 psi up to 15,000 or so psi, and often conveniently 2500 to 5000 psi. The sum of the carbon monoxide and hydrogen pressures often constitute approximately the total pressure, and the aforesaid ranges apply to this sum. Concentrations of catalyst can be used within broad ranges, with parameters similar to those for other cobalt-catalyzed carbonylation reactions, with concentrations usually being in the range of $10^{-6}$ to $10^{-1}$ moles/liter based on cobalt. The tertiary phosphine oxide will usually be present in excess, on a mole basis, of the cobalt, but will have value when employed over broad ranges, e.g. the range of 0.1:1 to 1000:1 molecules of the phosphine oxide to cobalt atom, and will usually be used in the range of 1:1 to 100:1 on the aforesaid basis. The carbonylation temperatures can vary widely, but will usually be selected to give desirable rates, and often will be in the range of 150° to 250° C.

The carbonylation will be conducted for a sufficient time to achieve desired conversions, which in batch reactions may be in the range of about 1 to 5 or so hours to achieve fairly high levels of conversion, depending upon temperature, pressure, catalyst activity and concentration, and other factors affecting carbonylation rates in known manner. Continuous processes are also contemplated in which a product stream is removed on an intermittent or continuous basis during the carbonylation.

Example

A one gram quantity of Co(acetate)$_2$. 4H$_2$O and 9 grams triphenylphosphine oxide were charged to an autoclave with 100 cc methanol and 30 cc methylnaphthalene. The reactor was pressured to 3200 psi with an approximately equimolar mixture of hydrogen and carbon monoxide and heated to 180° C. with stirring. The reaction was allowed to proceed for 5 hours. The reactor was cooled and vented, and the reaction product was analyzed and shown to contain ethanol (21.3%), methyl acetate (9.8%), dimethylacetal (15.9%) and acetic acid (5.1%). The products were distilled and the cobalt remained in a soluble form in the distillation residue which consisted primarily of methylnaphthalene. The absence of a solid coating or precipitate on the distillation flask was noted. The distillation residue was returned to the reactor with additional methanol, and found to display high catalytic activity under carbonylation conditions as employed in this example. Thus it is demonstrated that the catalyst can be retained in soluble form by use of phosphine oxide stabilizer, and recycled in a form suitable for use upon application of carbonylation conditions. Similar results to the foregoing can be obtained if tributylphosphine oxide or other tertiary phosphine oxides are substituted for the triphenylphosphine oxide.

A procedure was carried out utilizing the same components as Example 1, except that the phosphine oxide was omitted, and pressuring to 3600 psi, and employing a reaction time of 3½ hours. The reaction product included ethanol (15.6%), methylacetate (6.9%) and the dimethylacetal of acetaldehyde (5.1%). The product was distilled and the low boiling organic products removed, leaving a distillation heel which was primarily methylnaphthalene. The distillation flask became coated with a purple solid during distillation which was shown to be cobalt acetate.

It is known that some cobalt carbonyl compounds are volatile and also tend to be unstable unless a carbon monoxide atmosphere is maintained. This presents problems in distillation from mixtures containing cobalt carbonyl. If the cobalt carbonyl decomposes, the catalyst is lost as metal which precipitates. In the present procedure it has been found that the catalyst becomes oxidized during the distillation to cobalt (II) acetate, forming this salt with acetic acid produced in the reaction. This salt will precipitate unless a stabilizing component is present to form soluble cobalt (II) complexes. The complexes formed in the presence of the tertiary phosphine oxides are readily reformed into active cobalt carbonyl catalyst when treated with synthesis gas under pressure. It is to be noted that tertiary phosphine oxides, if present, have the desired effect regardless of what the mode of action may be, and this discovery in its broadest aspects is part of the invention. However it appears that the cobalt catalyst is converted to a cobalt (II) form and that this form is stabilized in some kind of complex in which the phosphine oxide takes part. When acetic acid or other acids are present, the cobalt (II) will generally be in the form of a salt of the acid, which lends itself to formation of a complex with the phosphine oxide. The phosphine oxide stabilizer also avoids the precipitation of cobalt metal, which generally occurs to some extent from decomposition of cobalt carbonyl upon heating under distillation conditions.

The distillation of the products of the present carbonylation reaction can conveniently be effected at atmospheric pressure. Higher or lower pressures can be used, but there may be no real advantage of vacuum distillation as the products are relatively low boiling. The reactor can simply be cooled and vented to relieve pressure, and the temperature gradually raised as the distillation proceeds to fractionate the products. Problems of cobalt carbonyl volatilization are not generally encountered at the temperatures needed. If desired, special procedures can be used, such as addition of air, to accelerate oxidation to a cobalt (II) form, but this is not necessary. Similarly, the venting of the carbon dioxide can be controlled along with temperature to avoid undue decomposition of the cobalt carbonyl with precipitation of cobalt metal, but ordinarily simply cooling and venting is sufficient.

The tertiary phosphine oxide serves its primary purpose during the distillation of the products, but its presence during the reaction apparently does not hinder the carbonylation in that comparable rates are obtained with and without the phosphine oxide. In any event the results demonstrate that the phosphine oxide may suitably be present during the carbonylation. While in principle it appears that the tertiary phosphine oxide can be added just prior to the distillation, this practice is not apt to be used as the catalyst recycle would ordinarily provide the phosphine oxide to the reactor for the carbonylation procedure. Acetic acid is produced in the reaction in minor amount, thereby providing acid to form a cobalt (II) salt during the distillation. If desired, additional acid can be added for this purpose, but it is not necessary. The acetic acid produced can be distilled and recovered as product, but can if desired be recycled in whole or part with the cobalt material for the next carbonylation cycle, although presence of acids may have some adverse effect upon catalyst activity. Ethanol, methyl acetate and acetaldehyde or its acetals can be recovered in the distillation, as separate products if desired, utilizing conventional distillation fractionation procedures in conjunction with the present invention, and the methyl acetate can, of course, be hydrolyzed if desired. The carbonylation process can to some extent be directed toward particular products at the expense of others by choice of process conditions. Ethanol is one of the main products of interest and in one aspect the present invention is particularly directed to its production and separation as the major product.

Water is produced in the reaction and will generally be separated by distillation prior to catalyst recycle, although it is not necessary to carefully remove all water from the reaction mixture.

The carbonylation is preferably carried out in the presence of a high boiling solvent which keeps the cobalt complex in solution when the products are distilled from the reaction mixture. High boiling organic solvents are suitable, particularly hydrocarbon solvents which boil at sufficiently high temperatures to permit facile distillation of ethanol, water and acetic acid therefrom. High boiling aromatic solvents are particularly suitable, e.g. naphthalene, methylnaphthalene, etc. High boiling aliphatic hydrocarbons can also be used, e.g. decane, dodecane, etc. In general it is preferred that the solvents be inert, but the presence of non-interfering substituents is not precluded. High boiling esters are suitable. Carbonylation can be conducted in the absence of such solvents, but the solvent serves to keep the cobalt component in solution as a distillation residue when the product is distilled. If desired, the tertiary phosphine oxide can serve as a high boiling solvent, and use of other solvents can be dispensed with. In such case it may be desirable to use a considerable excess of the phosphine oxide. The high boiling solvents useful herein include materials which are ordinarily solids but converted to liquids upon heating, as in the contemplated distillation procedure.

What is claimed:

1. In the process for the carbonylation of methanol with carbon monoxide and hydrogen in liquid phase at temperatures in the range of 150° to 250° C. and pressures in the range of 1500 to 15,000 psi in the presence of a cobalt carbonyl catalyst, the improvement which comprises conducting the carbonylation in the presence of a tertiary phosphine oxide, so as to have the tertiary phosphine oxide present as a catalyst stabilizer for product recovery, the tertiary phosphine oxide being a pentavalent phosphorus compound with three hydrocarbyl substituents on the phosphorus bonded by carbon-to-phosphorus bonds and separating the carbonylation products from the carbonylation reaction mixture by distilling in the presence of said tertiary phosphine oxide.

2. The process of claim 1 in which a triarylphosphine oxide is present.

3. The process of claim 1 in which a trialkylphosphine oxide is present.

4. The process of claim 1 in which triphenylphosphine oxide is present.

5. The process of claim 1 in which the cobalt catalyst is present in concentrations of $10^{-6}$ to $10^{-1}$ moles/liter and the tertiary phosphine oxide is present in 0.1:1 to 1000:1 ratio to cobalt.

6. The process of claim 5 in which the tertiary phosphine oxide is present in excess of the cobalt.

7. The process of claim 1 in which carbonylation at elevated temperature and pressure, is followed by cooling and venting and distillation of the products from the carbonylation reaction mixture at atmospheric pressure.

8. The process of claim 1 in which ethanol is the major product produced and separated from the reaction mixture.

9. The process of claim 1 in which the cobalt material in the distillation residue is recycled for further effective utilization in the cobaltcarbonyl catalyzed carbonylation in the said process.

10. The process of claim 9 in which ethanol is the major product recovered.

11. A process for separation of carbonylation products from a carbonylation reaction mixture containing cobalt compounds which is produced in the carbonylation of methanol with a cobalt carbonyl catalyst, which comprises distilling the products from said carbonylation reaction mixture containing a tertiary phosphine oxide in which three hydrocarbyl substituents are on the phosphorus.

12. The process of claim 11 in which the reaction mixture contains a high boiling inert organic solvent.

13. The process of claim 11 in which the reaction mixture contains a high boiling aromatic solvent.

14. The process of claim 11 in which ethanol is separated by distillation.

15. The process of claim 14 in which the reaction mixture contains a trialkylphosphine oxide.

16. The process of claim 14 in which the reaction mixture contains a triarylphosphine oxide.

17. The process of claim 16 in which the reaction mixture contains a high boiling aromatic solvent.

* * * * *